United States Patent
Ko et al.

(10) Patent No.: US 8,912,231 B2
(45) Date of Patent: Dec. 16, 2014

(54) METHOD OF TREATING AIRWAY REMOLDING SYMPTOM

(71) Applicant: Kaohsiung Medical University, Kaohsiung (TW)

(72) Inventors: Ying-Chin Ko, Kaohsiung (TW); Po-Lin Kuo, Kaohsiung (TW)

(73) Assignee: Kaohsiung Medical University, Kaohsiung (TW)

( * ) Notice: Subject to any disclaimer, the term of this patent is extended or adjusted under 35 U.S.C. 154(b) by 117 days.

(21) Appl. No.: 13/919,563

(22) Filed: Jun. 17, 2013

(65) Prior Publication Data
US 2013/0281543 A1    Oct. 24, 2013

Related U.S. Application Data

(63) Continuation of application No. 13/245,511, filed on Sep. 26, 2011, now abandoned.

(30) Foreign Application Priority Data

Jul. 18, 2011  (TW) .............................. 100125272 A

(51) Int. Cl.
| | | |
|---|---|---|
| *A61K 8/42* | (2006.01) | |
| *A61Q 7/00* | (2006.01) | |
| *C07C 69/18* | (2006.01) | |
| *A61K 31/12* | (2006.01) | |

(52) U.S. Cl.
CPC ..................................... *A61K 31/12* (2013.01)
USPC ......................................................... 514/546

(58) Field of Classification Search
USPC ......................................................... 514/546
See application file for complete search history.

(56) References Cited

U.S. PATENT DOCUMENTS

| | | |
|---|---|---|
| 6,482,421 B2 | 11/2002 | Weidner |
| 6,534,086 B1 | 3/2003 | Krumhar |
| 7,452,557 B2 | 11/2008 | Yoshida |
| 7,563,768 B2 | 7/2009 | Nakamura et al. |
| 7,919,584 B1 | 4/2011 | Belmares et al. |
| 2009/0220624 A1 | 9/2009 | Larkins |

FOREIGN PATENT DOCUMENTS

TW    I282281    6/2007

OTHER PUBLICATIONS

Sabina et al., 6-Shogaol inhibits monosodium urate crystal-induced inflammation—An in vivo and in vitro study, Food and Chemical Toxicology 48:229-235, Jan. 2010.*
Kuo et al., Ginger Suppresses Phthalate Ester-Induced Airway Remodeling, Journal of Agricultural and Food Chemistry, Journal of Agricultural and Food Chemistry, 59, 3429-3438, 2011.*
Kuo, et al., "Ginger Suppresses Phthalate Ester-Induced Airway Remodeling", Journal of Agricultural and Food Chemistry, (2011), pp. 3429-3438, vol. 59.

* cited by examiner

*Primary Examiner* — Jeffrey S. Lundgren
*Assistant Examiner* — Zenab Olabowale
(74) *Attorney, Agent, or Firm* — Muncy, Geissler, Olds & Lowe, P.C.

(57) ABSTRACT

A method of treating airway remodeling symptom caused by phthalate esters, by providing a medication comprising: a ginger compound selected from one of (a) [6]-shogaol, (b) [6]-shogaol and [10]-gingerol, (c) [6]-shogaol and [8]-gingerol, and (d) [6]-shogaol and [6]-gingerol, and an acceptable carrier or excipient, which can relieve the airway remodeling symptoms of asthma, particularly to phthalate ester-induced airway remodeling, by suppressing the proliferation and migration of bronchial smooth muscle cells and reducing the instances of fatal asthma.

2 Claims, 6 Drawing Sheets

US 8,912,231 B2

METHOD OF TREATING AIRWAY REMOLDING SYMPTOM

CROSS REFERENCE TO RELATED APPLICATIONS

This is a continuous application of U.S. patent application Ser. No. 13/245,511 filed on Sep. 26, 2011.

BACKGROUND OF THE INVENTION

1. Field of the Invention

The present invention relates to a method of treating airway remodeling symptom, particularly to a method of treating airway remodeling symptom caused by phthalate esters.

2. Description of the Related Art

Asthma is a common chronic inflammatory airway disease and is characterized by serious trachea inflammation, trachea hyperreactivity, and airway remodeling. It is reported that the airway remodeling symptom of asthma usually comes accompany with severe inflammation which is induced by allergies-sensitized epithelial cells, with the secretion of inflammatory factors in bronchial epithelial cells, such as cytokines or chemokine, increasing the proliferation and migration of bronchial smooth muscle cells. Wherein, according to current reports, the secretion of interleukin-8 (IL-8) and regulated on activation normal T cell expressed and secreted (RANTES) plays a crucial role in airway remodeling, and which will lead to the increase of bronchial smooth muscle mass, angiogenesis, subepithelial fibrosis, submucosal gland enlargement and the loss of epithelial integrity.

In general, asthma is more severe and less responsive to treatment in certain people who suffer from airway remodeling. The airway remodeling will result in permanent structural changes in airway tissues, airway wall thickness and vascularituy, and finally increase the instances of persistent and fetal asthma attacks. In current medicine, conventional medications for therapy or prophylaxis of asthma includes corticosteroids, leukotriene response modifiers and β2-agonists, wherein the corticosteroids are a quick-relief asthma medication, being capable of relieving the respiratory tract and the symptoms of asthma via increasing the transcription of anti-inflammatory protein, and inhibiting the inflammation and the transcription of pro-inflammatory protein. Yet, the pharmaceutics effects of leukotriene response modifiers are mainly on inhibiting the eosionophil and mast cell to secrete leukotrienes which are fatty signaling molecules and capable of increasing the secretion of mucus and bronchoconstriction. With the treatment of the leukotriene response modifiers, it is efficient to moderate the secretion of mucus. Finally, the β2-agonists can bind to β2-adrenoreceptors of smooth muscle cells and lead to tracheaectasy.

The conventional medication only can improve the acute symptoms of asthma by reducing the inflammation of bronchial tracts or increasing tracheaectasy, and however, the conventional medications are less effective in treating of airway remodeling symptom usually happened in the late or medium phase of asthma. Furthermore, the conventional medications generally consist of artificial chemicals, and which may leads to serious side effects after long-term of treatments, such as liver toxicity.

Hence there is a need of providing a new medication for therapy or prophylaxis of asthma, for the sake of effectively improving the airway remodeling symptom and avoiding the aggravation of condition of asthma, especially in late or medium phase of asthma.

SUMMARY OF THE INVENTION

The primary objective of this invention is to provide a method of treating airway remodeling symptom, which can suppress the proliferation and migration of bronchial smooth muscle cells and prevent from severely dyspnea.

The secondary objective of this invention is to provide a method of treating airway remodeling symptom, which comprises ginger compounds and capable of being used in suppressing the proliferation and migration of bronchial smooth muscle cells.

A method of treating airway remodeling symptom caused by phthalate esters, by providing a medication comprising: a ginger compound selected from one of (a) [6]-shogaol, (b) [6]-shogaol and [10]-gingerol, (c) [6]-shogaol and [8]-gingerol, and (d) [6]-shogaol and [6]-gingerol, and an acceptable carrier or excipient.

Further scope of the applicability of the present invention will become apparent from the detailed description given hereinafter. However, it should be understood that the detailed description and specific examples, while indicating preferable embodiments of the invention, are given by way of illustration only, since various more will become apparent to those skilled in the art from this detailed description.

BRIEF DESCRIPTION OF THE DRAWINGS

The present invention will become more fully understood from the detailed description given herein below and the accompanying drawings which are given by way of illustration only, and thus are not limitative of the present invention, and wherein.

All figures are drawn for ease of explaining the basic teachings of the present invention only; the extensions of the figures with respect to number, position, relationship, and dimensions of the parts to form the preferred embodiment will be explained or will be within the skill of the art after the following teachings of the present invention have been read and understood. Further, the exact dimensions and dimensional proportions conforming to specific force, weight, strength, and similar requirements will likewise be within the skill of the art after the following teachings of the present invention have been read and understood.

DETAILED DESCRIPTION OF THE INVENTION

The present invention relates to a method of treating airway remolding symptom caused by phthalate esters, by providing a medication comprising: a ginger compound selected from one of (a) [6]-shogaol, (b) [6]-shogaol and [10]-gingerol, (c) [6]-shogaol and [8]-gingerol, and (d) [6]-shogaol and [6]-gingerol, and an acceptable carrier or excipient, by suppressing the proliferation and migration of bronchial smooth muscle cells and improve the dyspnea. Accordingly, with the method of the present invention, the symptoms, as well as the progression of asthma will be significantly repressed.

With reference to FIGS. 1 to 4, the chemical structures of ginger compounds including [6]-shogaol, [6]-gingerol, [8]-gingerol and [10]-gingerol are shown respectively. In the present invention, the ginger compounds are but not limit to obtain from the extract of ginger (Zingiber officnale), ginger roots for example, peppers or chili. The ginger compounds of the present invention can also be obtained by artificially synthesizing. As an example, the [6]-shogaol used in the present invention is obtained from a ginger extract, and the [6]-gingerol is obtained via a dehydration of [6]-shogaol.

For the sake of proving the effect of the medication on asthma, a phthalate ester-treated bronchial smooth muscle cell line is prepared to carry out a trial of the present invention, in which a phthalate ester-treated bronchial epithelial cell line is prepared and coincubated with a bronchial smooth muscle cell line to generate the phthalate ester-treated bronchial smooth muscle cell line, and the pathological data of the phthalate ester-treated bronchial smooth muscle cells, for example cell proliferation or cell migration under each condition, are demonstrated and monitored.

Figure 1:
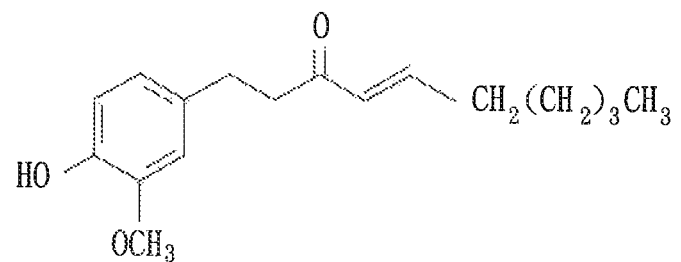
FIG. 1 is a diagram illustrating the structure of [6]-shogaol in the present invention.
Figure 2:
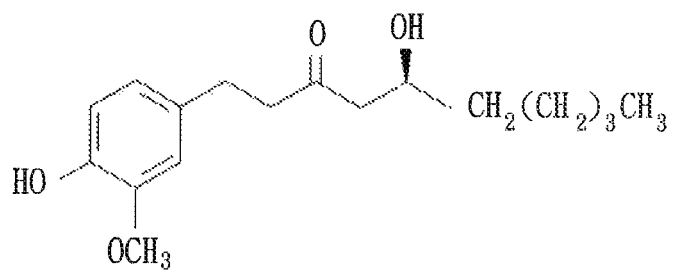
FIG. 2 is a diagram illustrating the structure of [6]-gingerol in the present invention.
Figure 3:
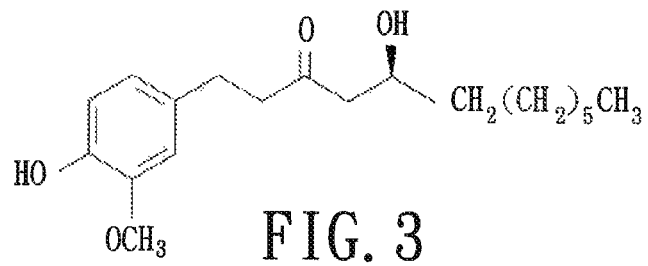
FIG. 3 is a diagram illustrating the structure of [8]-gingerol in the present invention.
Figure 4:
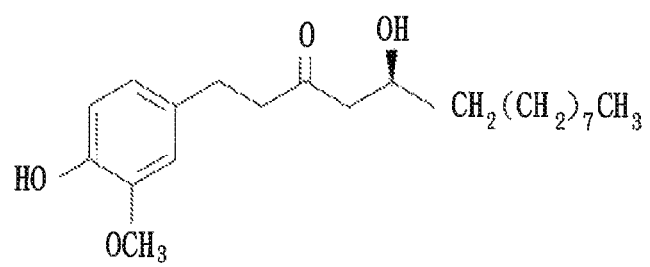
FIG. 4 is a diagram illustrating the structure of [10]-gingerol in the present invention.
Figure 5:
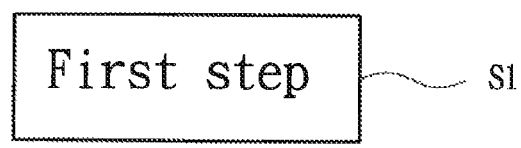
FIG. 5 is a flowchart illustrating a trial of PE induced airway remodeling of the present invention.
Figure 5:
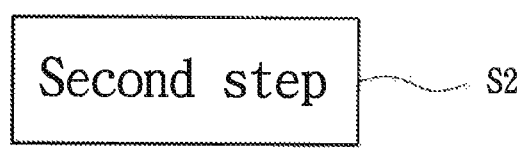

With reference to FIG. 5, the phthalate ester-treated bronchial smooth muscle cells are prepared by processing two steps. In the first step, a phthalate ester-treated bronchial epithelial cell line is obtained by harvesting a human bronchial epithelial cell line in a phthalate ester at 37±1° C. for 6 hours, with each 100 mm incubating plate receiving $2 \times 10^6$ cells and with the treatment of the phthalate ester to induce the excretion of proinflammatory cytokines in the human bronchial epithelial cell line, such as IL-8 and RANTES, followed by removing the phthalate ester from the human bronchial epithelial cell line, reincubating the human bronchial epithelial cell lines in a culturing medium for 24 hours, and finally collecting the supernatants to obtain plasticizers-treated bronchial epithelial cells of the present invention. In specification, the phthalate ester of the present invention can be selected from a group of butylbenzyl phthalate (BBP), bis-(2-ethylhexyl) phthalate (BEHP), dibutyl phthalate (DBP) and diethyl phthalate (DEP), and with the concentration of 0.1 to 5.0 µM.

In the second step, the phthalate ester-treated bronchial epithelial cells obtained from the first step are coincubated with a human bronchial smooth muscle cell line to obtain the phthalate ester-treated bronchial smooth muscle cells of the present invention. In specification, primary human bronchial smooth cells (BSMC) purchased from Lonza are prepared and cocultured in SmGM-2 smooth muscle medium (Lonza) with the phthalate ester-treated bronchial epithelial cells at 37±1° C. for 72 hours, with such arrangement inducing the cell proliferation and migration of the human bronchial smooth muscle cell lines and obtaining the phthalate ester-treated bronchial smooth muscle cells of the present invention.

In the first embodiment of the present invention, a human bronchial epithelial cell line, BEAS-2B (CRL-9609), purchased from American Type Cell Collection (ATCC), is prepared and precultured in bronchial epithelial growth medium (BRAS medium; Lobza, Walkersville, Md.), and then coincubated with 5 µM DBP to obtained DBP-treated BEAS cells.

With reference of TABLE 1, the BSMCs are previously seeded into a migration chamber for 24 hours, with the BSMCs placing on the surface of the migration chamber, and randomly assigned into 10 groups including A1-1 to A1-10 to carry out various treatments between 10 groups. In groups A1-1 to A1-5, BSMCs are coincubated in dimethyl sulfoxide (DMSO), [6]-shogaol, [6]-gingerol, [8]-gingerol or [10]-gingerol, yet in groups A1-6 to A1-10, BSMCs are coincubated in DMSO, [6]-shogaol, [6]-gingerol, [8]-gingerol or [10]-gingerol and then cocultured with DBP-BEAS for 24 hours. After the treatments, the BSMCs of the groups A1-1 to A1-10 are analyzed by a QCM Chemotaxis 8 µm cell migration assay system (Chemicon, Temecula, Calif.; Millipore Corp, Bedford, Mass.), with the BSMCs in each group being stained, lysed and finally quantified on a microplate at 560 nm in specification the ginger compounds, such as [6]-shogaol, [6]-gingerol, [8]-gingerol or [10]-gingerol, used in the present embodiment are all collected from Sigma Chemical Co. (St. Louis, Mo.), and dissolved in DMSO at a concentration of 5 µM before using in coincubation.

TABLE 1

Groups arrangement of cell migration trial

| Groups | DBP-BEAS | Treatments |
|--------|----------|------------|
| A1-1   | +        | DMSO       |
| A1-2   | +        | [6]-shogaol |
| A1-3   | +        | [6]-gingerol |
| A1-4   | +        | [8]-gingerol |
| A1-5   | +        | [10]-gingerol |
| A1-6   | −        | DMSO       |
| A1-7   | −        | [6]-shogaol |
| A1-8   | −        | [6]-gingerol |
| A1-9   | −        | [8]-gingerol |
| A1-10  | −        | [10]-gingerol |

Additionally with reference to TABLE 2, the BSMCs are placed and preincubated in 96-well culture plates for 24 hours, followed by randomly assigning into 10 groups including A2-1 to A2-10 to carry out various treatments between 10 groups. In groups A2-1 to A2-5, BSMCs are coincubated in dimethyl sulfoxide (DMSO), [6]-shogaol, [6]-gingerol, [8]-gingerol or [10]-gingerol, yet in groups A2-6 to A2-10, BSMCs are coincubated in DMSO, [6]-shogaol, [6]-gingerol, [8]-gingerol or [10]-gingerol for 1 hours and then cocultured with DBP-BEAS for 72 hours. After the various treatments of each group, the proliferation degrees of BSMCs in each group are determined by Premixed WST-1 Cell Proliferation Reagent (Clontech Laboratories Inc., Mountain View, Calif.).

TABLE 2

Groups arrangement of cell migration trial

| Groups | DBP-BEAS | Treatments |
|--------|----------|------------|
| A2-1   | +        | DMSO       |
| A2-2   | +        | [6]-shogaol |
| A2-3   | +        | [6]-gingerol |
| A2-4   | +        | [8]-gingerol |
| A2-5   | +        | [10]-gingerol |
| A2-6   | −        | DMSO       |
| A2-7   | −        | [6]-shogaol |
| A2-8   | −        | [6]-gingerol |
| A2-9   | −        | [8]-gingerol |
| A2-10  | −        | [10]-gingerol |

Figure 6:
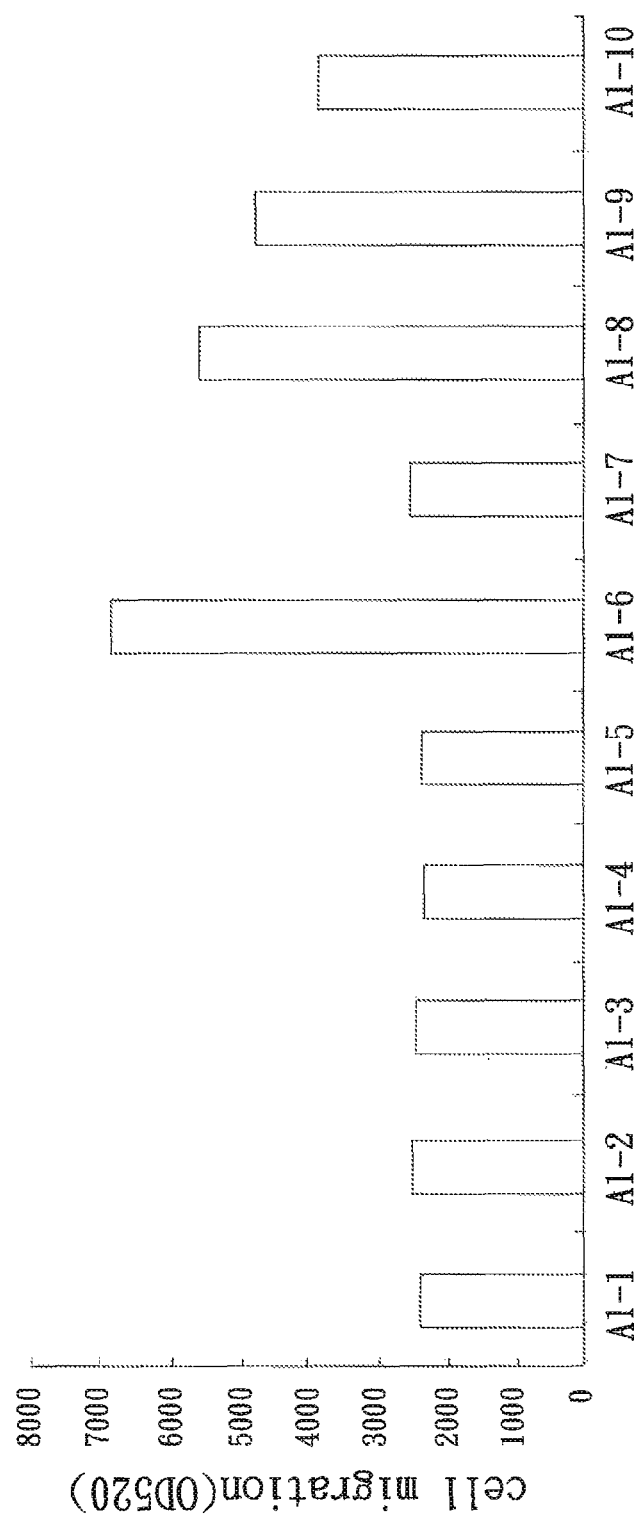
FIG. 6 is a bar chart illustrating the migration of cells of groups A1-1 to A1-10.
Figure 7:
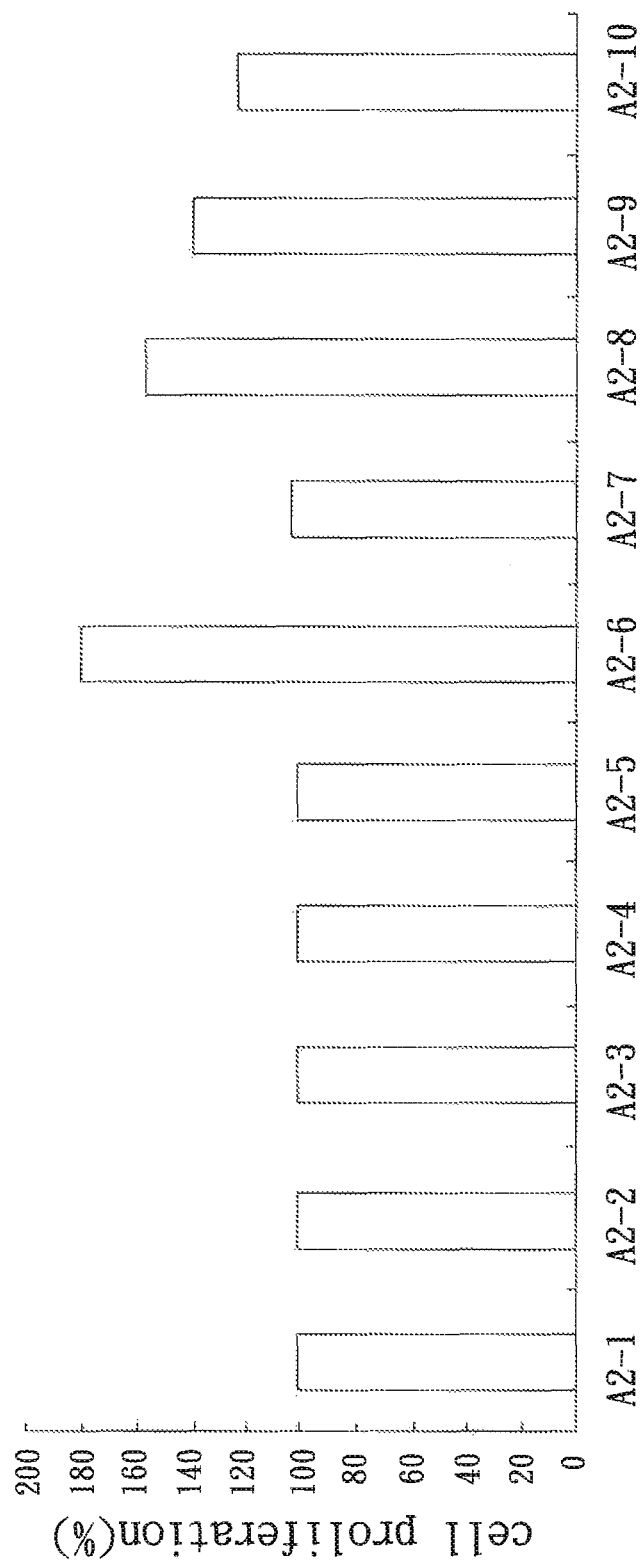
FIG. 7 is a bar chart illustrating the proliferation of cells of groups A2-1 to A2-10.

In FIGS. 6 and 7, the phthalate ester-induced pathological data of the MSMCs in the groups A1-1 to A1-10 and A2-1 to 2-10 are shown. It is noted that the phthalate ester will lead to the airway remodeling of the bronchial smooth muscle cells, as the hyperplasia and hypertrophy of the bronchial smooth muscle cells being observed in data A1-6 and A2-6. However, with the treatments of ginger compounds of the present invention, the phthalate ester-induced airway remodeling can be significantly suppressed and relieved (see data A1-7 to A1-10 and A2-7 to A2-10). Also, the treatments of the ginger compounds will not cause any negative effects to the bronchial smooth muscle cells, as the data of groups A1-1 to A1-5 and A2-1 to A2-5 being no different from normal.

Hence, it is demonstrated that the ginger compounds, including [6]-shogaol, [6]-gingerol, [8]-gingerol and [10]-gingerol, are sufficient in suppressing the phthalate ester-induced airway remodeling.

In a second embodiment, another human bronchial epithelial cell lines, HBE135-E6E7 (HBE, CRL-2741), purchased from American Type Cell Collection (ATCC) is prepared and precultured in keratinocyte serum-free medium (K-SF medium), with the serum-free medium comprising 5 ng/ml human recombinant EGF and 0.05 mg/ml, bovine pituitary extract (Invitrogen) supplemented with 0.005 mg/mL insulin and 500 ng/mL hydrocortisone. In the present embodiment, the HBE cells are also coincubated with 5 μM DBP to obtained DBP-treated HBE cells.

In the present embodiment, all of the treatments and assays on the BSMCs are the same as that of the first embodiment, and the only difference between the first and the second embodiment is the phthalate ester-treated bronchial epithelial cell line used in the second embodiment is the DBP-treated HBE cells.

In TABLE 3 and 4, 20 groups of BSMCs in the second embodiment, including B1-1 to B1-1- and B2-1 to B2-10, as well as the various treatments thereof are summarized. In the second embodiment the BSMCs in groups B1-1 to B1-10 are analyzed by the QCM Chemotaxis 8 μm cell migration assay system and quantified at 560 nm, and the BSMCs in groups B2-1 to B2-10 are analyzed by Premixed WST-1 Cell Proliferation Reagent.

TABLE 3

Groups arrangement in the second embodiment

| Groups | DBP-HBE | Treatments |
| --- | --- | --- |
| B1-1 | + | DMSO |
| B1-2 | + | [6]-shogaol |
| B1-3 | + | [6]-gingerol |
| B1-4 | + | [8]-gingerol |
| B1-5 | + | [10]-gingerol |
| B1-6 | − | DMSO |
| B1-7 | − | [6]-shogaol |
| B1-8 | − | [6]-gingerol |
| B1-9 | − | [8]-gingerol |
| B1-10 | − | [10]-gingerol |
| B2-1 | + | DMSO |
| B2-2 | + | [6]-shogaol |
| B2-3 | + | [6]-gingerol |
| B2-4 | + | [8]-gingerol |

TABLE 3-continued

Groups arrangement in the second embodiment

| Groups | DBP-HBE | Treatments |
| --- | --- | --- |
| B2-5 | + | [10]-gingerol |
| B2-6 | − | DMSO |
| B2-7 | − | [6]-shogaol |
| B2-8 | − | [6]-gingerol |
| B2-9 | − | [8]-gingerol |
| B2-10 | − | [10]-gingerol |

Figure 8:
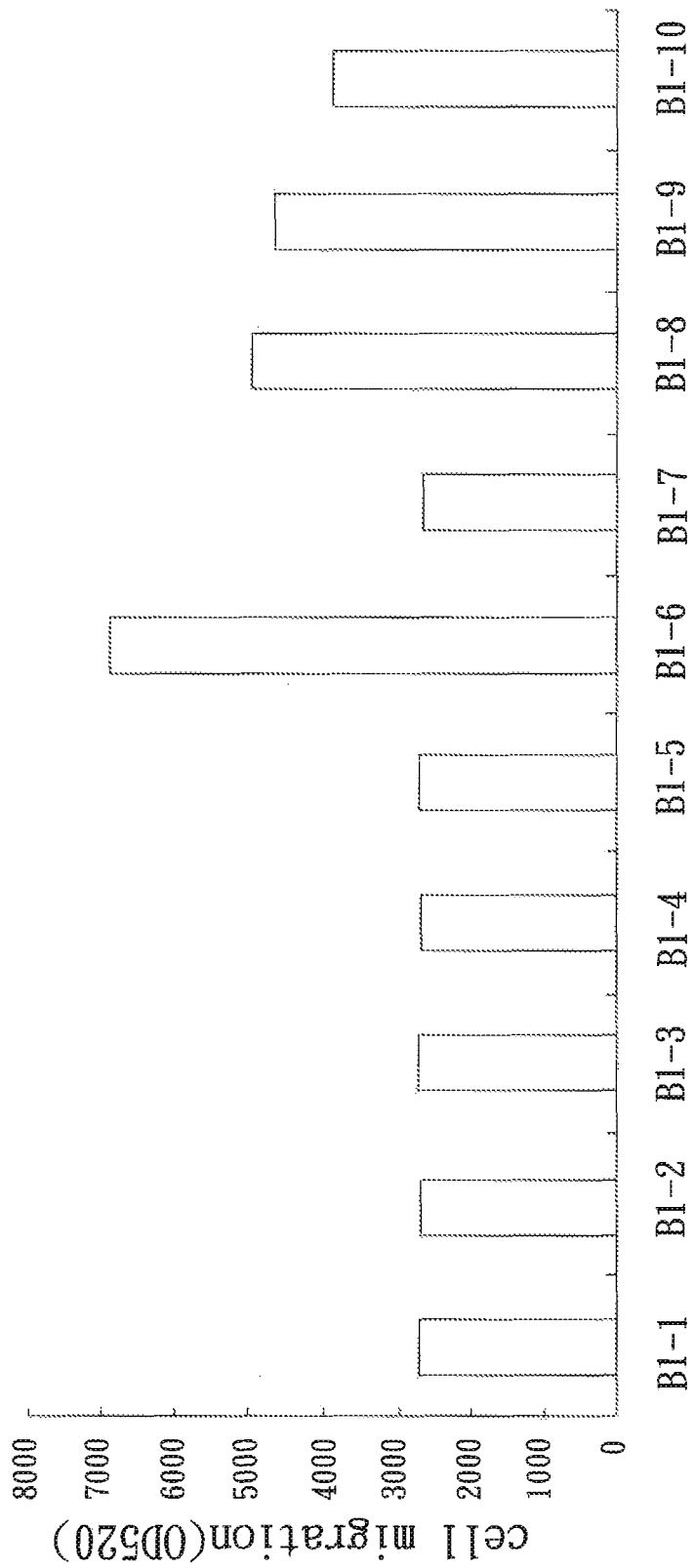
FIG. 8 is a bar chart illustrating the migration of cells of groups B1-1 to B1-10.
Figure 9:
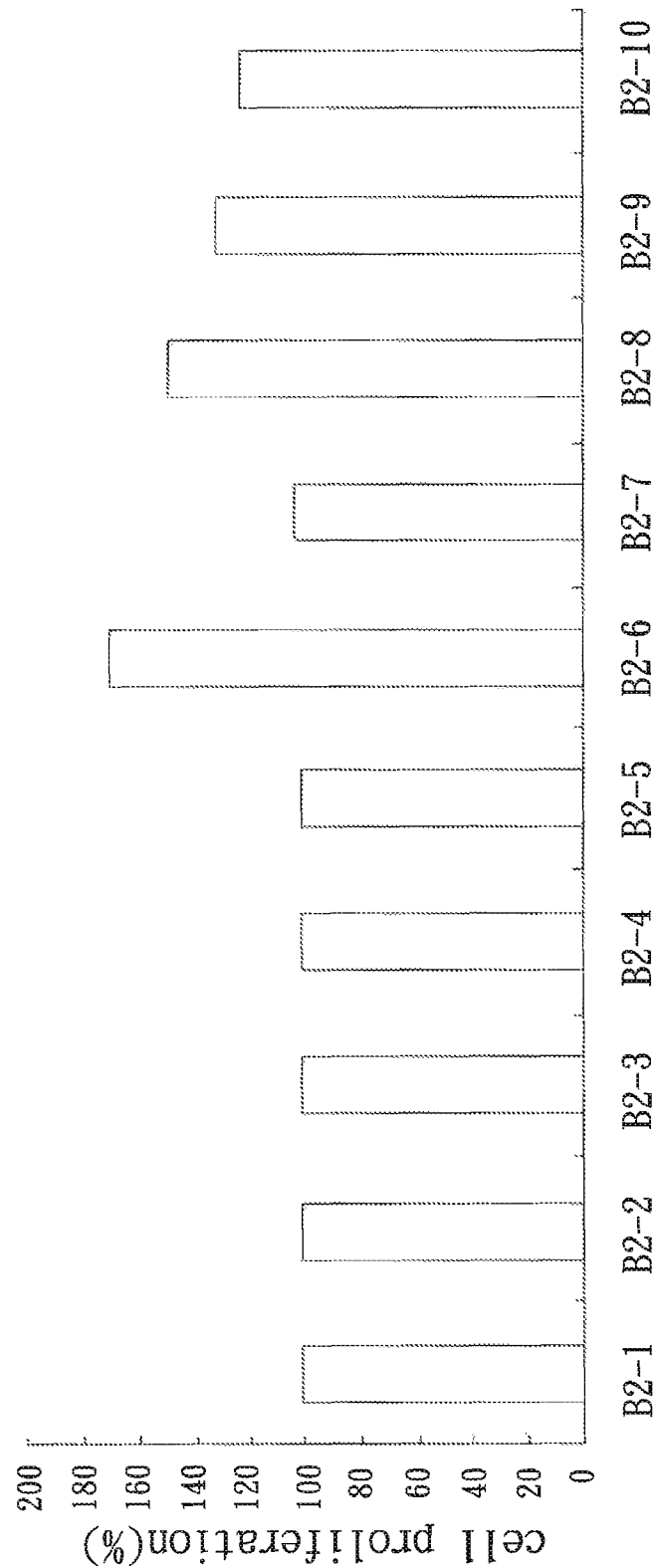
FIG. 9 is a bar chart illustrating the proliferation of cells of groups B2-1 to B2-10.

In FIGS. 8 and 9, the phthalate ester-induced pathological data of the MSMCs in the groups B1-1 to B1-10 and B2-1 to B-10 are shown. It is further demonstrated that the phthalate ester will induce the airway remodeling symptom, for example the increase in size and migration of the bronchial smooth muscle cells as being shown in data B1-6 and B2-6, and the treatments of the ginger compounds of the present invention can effetely improve the phthalate ester-induced symptoms and reduce the instances of fatal asthma. With the data in FIGS. 8 and 9, the effects of the ginger compounds on the therapy or prophylaxos of asthma are further validated.

Through the present invention, a method of treating airway remodeling symptom by providing a medication comprising a ginger compound, and an acceptable carrier or excipient, wherein the ginger compound is selected from one of (a) [6]-shogaol, (b) [6]-shogaol and [10]-gingerol, (c) [6]-shogaol and [8]-gingerol, and (d) [6]-shogaol and [6]-gingerol. The method of the present invention is sufficient to suppress the proliferation and migration of bronchial smooth muscle cells, and has no toxicity and negative effects to human, so that the method of the present invention is capable of being applied to patients who suffered from severely asthma or airway remodeling symptom.

Although the invention has been described in detail with reference to its presently preferred embodiment, it will be understood by one of ordinary skill in the art that various modifications can be made without departing from the spirit and the scope of the invention, as set forth in the appended claims.

What is claimed is:

1. A method of treating airway remodeling symptom caused by phthalate esters, by providing a medication to a subject in need thereof to suppress the proliferation and migration of bronchial smooth muscle cells, wherein the medication comprises:
   a ginger compound selected from one of (a) [6]-shogaol, (b) [6]-shogaol and [10]-gingerol, (c) [6]-shogaol and [8]-gingerol, (d) [6]-shogaol and [6]-gingerol, and
   an acceptable carrier or excipient.

2. The method of treating airway remodeling symptom caused by phthalate esters as defined in claim 1, wherein the phthalate esters includes butylbenzyl phthalate, bis-(2-ethylhexyl)phthalate, dibutyl phthalate, and diethyl phthalate.

\* \* \* \* \*